United States Patent [19]
Nardella

[11] Patent Number: 5,437,662
[45] Date of Patent: Aug. 1, 1995

[54] FLUID COOLED ELECTROSURGICAL CAUTERIZATION SYSTEM

[75] Inventor: Paul C. Nardella, North Easton, Mass.

[73] Assignee: American Cardiac Ablation Co., Inc., Taunton, Mass.

[21] Appl. No.: 197,959

[22] Filed: Feb. 17, 1994

Related U.S. Application Data

[63] Continuation of Ser. No. 975,801, Nov. 13, 1992, Pat. No. 5,342,357.

[51] Int. Cl.$^6$ ............................................. A61B 17/39
[52] U.S. Cl. ...................................... 606/40; 606/38; 606/39; 606/48; 606/50
[58] Field of Search ............................. 606/34, 37–40, 606/42, 45, 46, 48, 49, 50

[56] References Cited

U.S. PATENT DOCUMENTS

| | | |
|---|---|---|
| 1,983,669 | 4/1933 | Kimble . |
| 3,601,126 | 8/1971 | Estes ............................... 128/303.14 |
| 4,114,623 | 9/1978 | Meinke et al. . |
| 4,303,073 | 12/1981 | Archibald . |
| 4,474,179 | 10/1984 | Koch ............................... 606/38 X |
| 4,532,924 | 8/1985 | Auth et al. . |
| 4,637,392 | 1/1987 | Sorochenko et al. . |
| 4,674,499 | 6/1987 | Pao . |
| 4,805,621 | 2/1989 | Heinze et al. . |
| 4,862,889 | 9/1989 | Feucht . |
| 4,907,589 | 3/1990 | Cosman . |
| 4,931,047 | 6/1990 | Broadwin et al. ................ 606/42 X |
| 4,934,377 | 6/1990 | Bova et al. . |
| 4,943,290 | 7/1990 | Rexroth et al. . |
| 5,122,137 | 6/1992 | Lennox et al. ......................... 606/40 |
| 5,342,357 | 8/1994 | Nardella ................................ 606/40 |

FOREIGN PATENT DOCUMENTS

| | | | |
|---|---|---|---|
| 2903982 | 2/1981 | Germany | ........................ 606/46 |
| 2213381 | 8/1989 | United Kingdom | ............. 606/38 |

OTHER PUBLICATIONS

Sugita et al. "Bipolar Coagulator . . . Thermocontrol", J. Neurosurg., vol. 41., Dec. 1974, pp. 777–779.
Auth, "Endoscopic Heat Probe Coagulation".
Nardella, Paul C., "Radio Frequency Energy and Impedance Feedback", SPIE vol. 1068, Catheter-Based Sensing and Imaging Technology, pp. 42–48 (1989).
"Endoscopic Heat Probe Coagulation", David C. Auth, Ph.D., P.E.

Primary Examiner—Lee S. Cohen
Attorney, Agent, or Firm—Lahive & Cockfield; William C. Geary, III

[57] ABSTRACT

An electrosurgical probe is disclosed which provides the ability to both cut and cauterize tissue. The probe includes at least one cauterization electrode mounted upon a distal portion of the electrode and adapted to deliver electrosurgical energy to tissue. Further, a central lumen is disposed within the probe. The lumen is adapted to accommodate the flow of fluid from a remote source to tissue through an outlet port in the distal end of the probe. Also, the lumen houses a cutting electrode which is selectively deployable. Both cauterization and coagulation can be conducted in a bipolar mode. The flow of fluid through the lumen serves to limit the heat transfer from the cauterization electrode to adjacent tissue to an extent sufficient to prevent the sticking of tissue to the probe. A feedback system is also provided to optimize the electrode temperature.

4 Claims, 5 Drawing Sheets

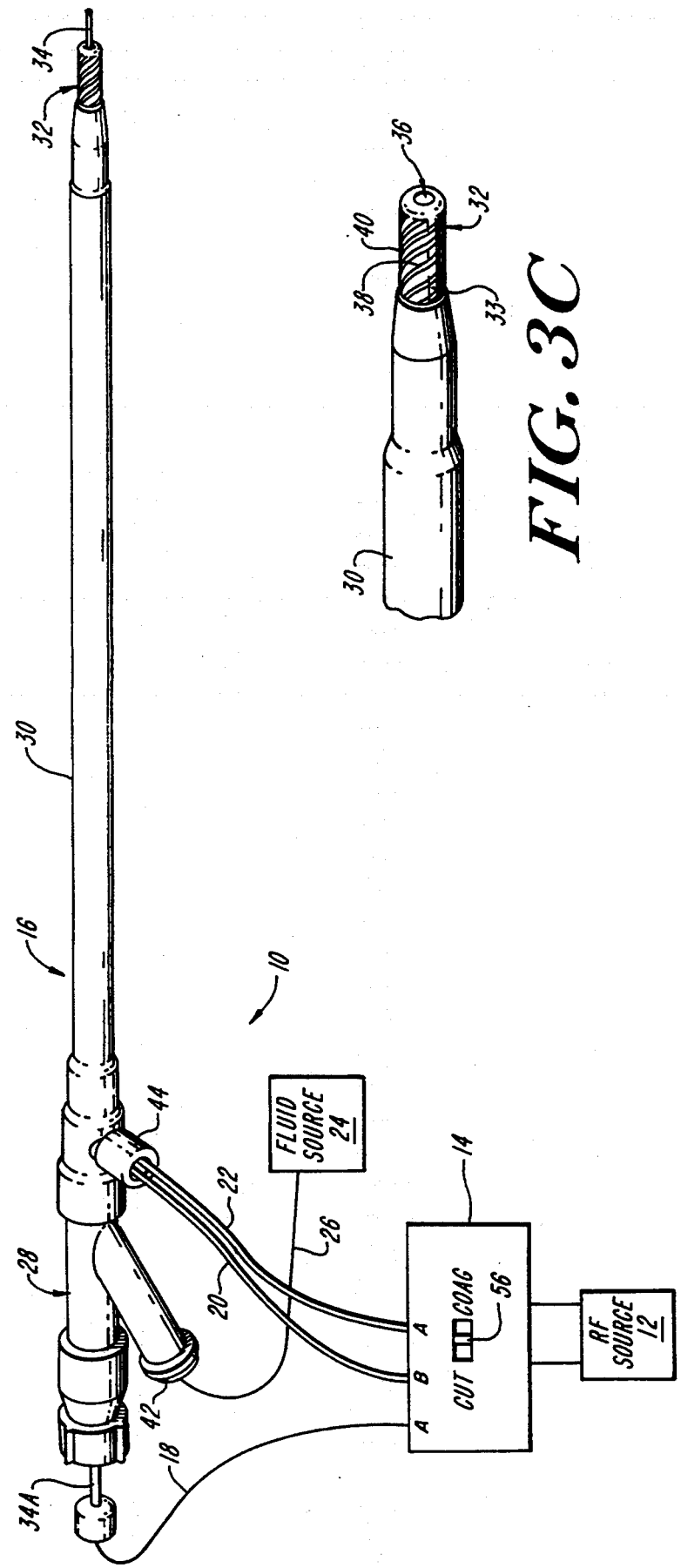

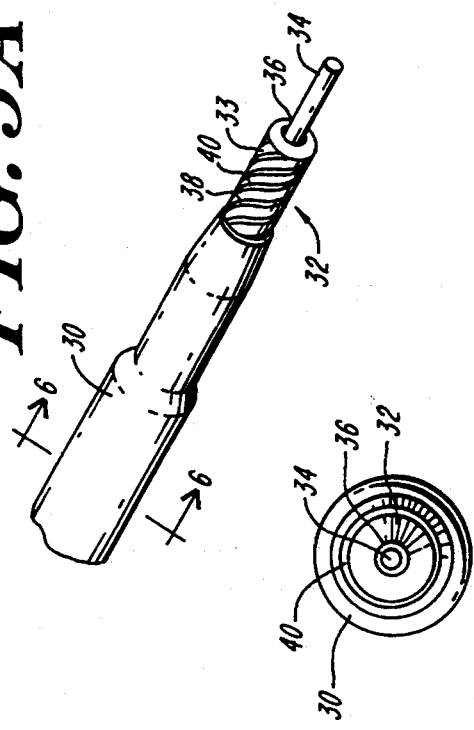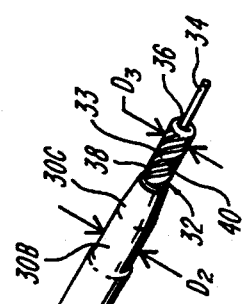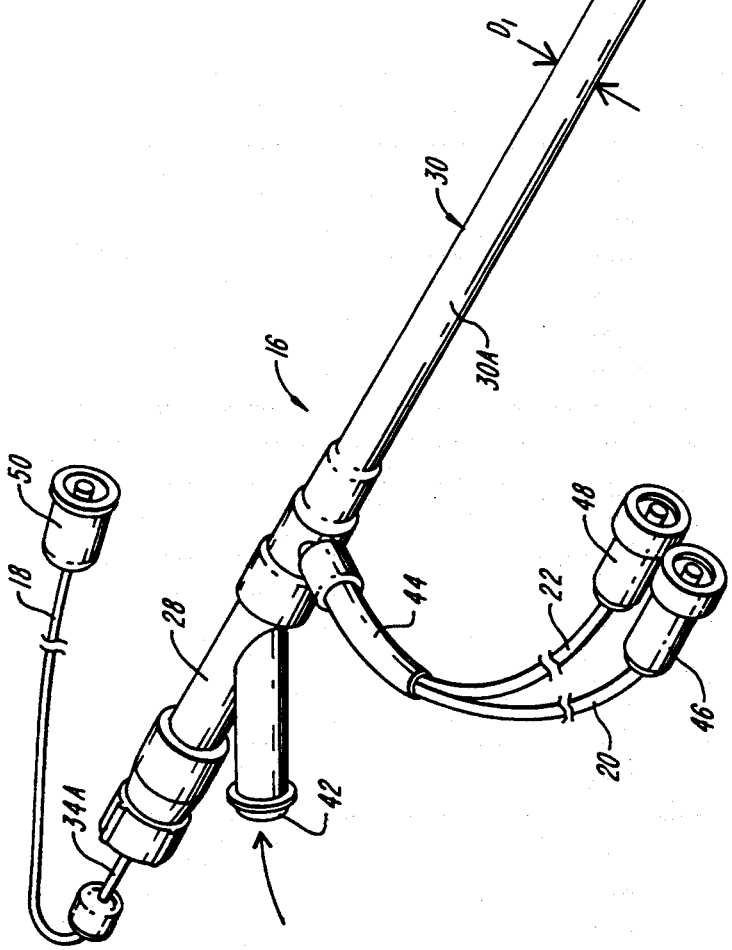

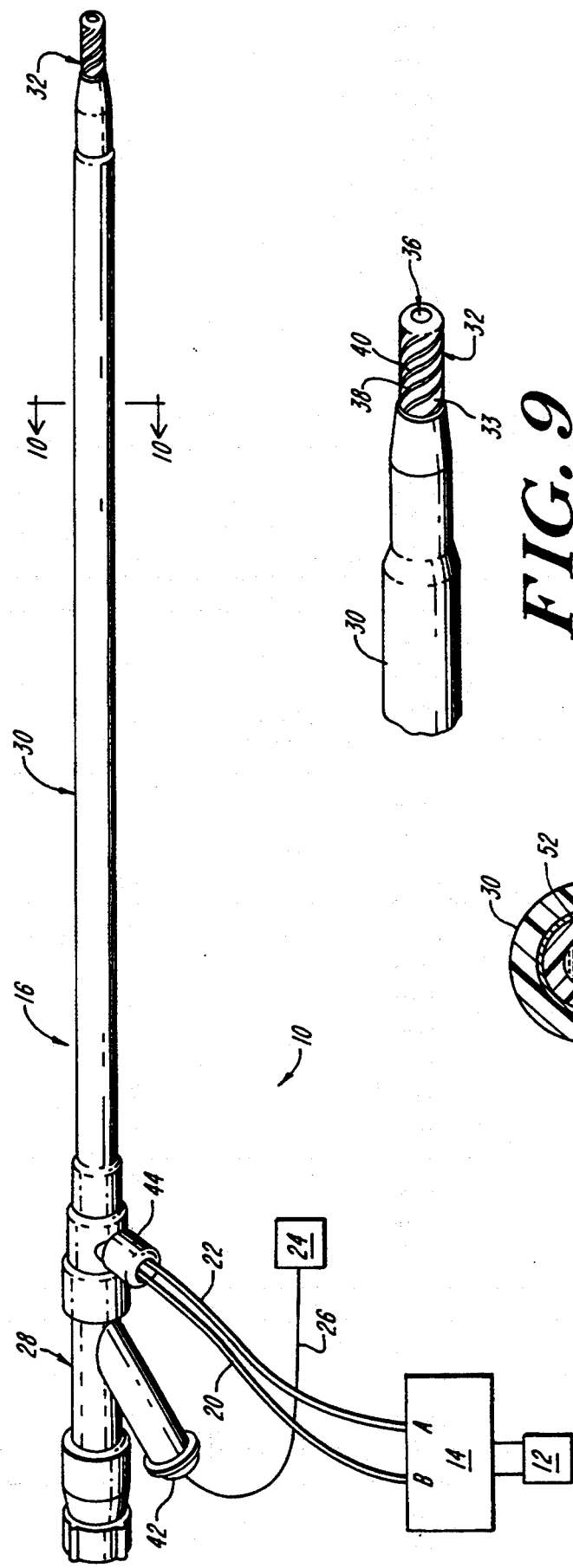

FLUID COOLED ELECTROSURGICAL CAUTERIZATION SYSTEM

This is a continuation of application Ser. No. 07/975,801 filed on Nov. 13, 1992, now U.S. Pat No. 5,342,357.

BACKGROUND OF THE INVENTION

The present invention relates generally to the field of electrosurgery. More particularly, the present invention relates to a system for controlling heat transfer from surgical electrodes to adjacent tissue.

During the course of surgical procedures it is often necessary to cauterize or coagulate tissue to control bleeding. Electrosurgical devices are known which utilize electrical current for tissue cauterization. U.S. Pat. Nos. 1,983,669 and 4,637,392 disclose electrical cauterization devices in which electrodes are disposed about the surface of a probe. Tissue is heated and coagulation is effected by delivering electrosurgical energy to tissue through the electrodes. Among the drawbacks of such devices is the potential that the electrodes will become overly heated, thus prematurely dessicating the tissue and causing the tissue to stick to the electrodes. This can result in further bleeding upon disengagement of the electrodes from the tissue, and the need to remove tissue from the electrode before continuing to use the device. Moreover, it can be inconvenient to use such cauterization devices during certain surgical procedures because cutting and cauterization must be performed with separate instruments.

Various electrosurgical probes exist for transferring energy to a biological site. Typically these probes dispose a metallic electrode along the outer surface of a rigid shaft. When the probe is positioned within the patient, the probe is in contact with the tissue at the surgical site. As energy is transferred through the electrode, electrical currents are established within adjacent tissue. As current passes through the tissue, some energy is absorbed into the tissue causing tissue temperature to rise. The rising temperature of the tissue denatures tissue protein molecules and facilitates coagulation.

Among the drawbacks of such devices is the potential that the electrodes will become overheated, and the denatured proteins will weld to the electrode on the outer surface of the probe. This can result in tissue searing or dessication, or in tissue being torn from the surgical site as the probe is removed from the patient. Such a tear can result in bleeding or the reopening of a wound. A further problem results from tissue collecting over the probe. Tissue stuck to the probe interferes with the delivery of energy to the surgical site. This interference limits the depth of penetration of energy into the tissue and thereby limits the depth of cauterization. Because of these drawbacks these devices are impractical for certain surgical procedures.

Surgical systems exist that attempt to limit the sticking of tissue to surgical probes. Some thermal cauterizing probes have placed a non-stick coating of teflon ® around the thermal electrode. However, because teflon does not conduct electricity the use of this technique for electrosurgical probes is impractical. Some electrosurgical systems monitor the temperature of the electrodes at the probe and reduce the energy being transferred to the site in order to control the temperature of the probe. This process results in a fluctuating energy density being delivered to the surgical site and a resulting uncertainty as to the depth of cauterization being effected.

There is a need for an electrosurgical device and system that can perform tissue cutting procedures and tissue cauterization procedures without overheating and causing tissue to stick or weld to the electrode. Such a device would be useful in that it would eliminate the need for the surgeon to scrape tissue and/or coagulant from the probe during the cauterization or cutting procedure. A device of this type would be well suited to general surgical procedures as well as to microsurgical procedures.

Accordingly, it is an object of the present invention to provide a surgical device and system that controls the transfer of heat from the device to tissue at the surgical site. A further object of the invention is to provide such a device that is adapted to control the temperature of an electrode mounted on an electrosurgical device. Yet another object of the invention is to provide an electrosurgical device that controls the transfer of heat from the electrode to adjacent tissue without limiting the electromagnetic energy delivered to the tissue. It is also an object of the invention to provide an electrosurgical device that prevents tissue and/or coagulant from welding to an energy delivering electrode. Other objects of the invention will be apparent upon reading the description which follows.

SUMMARY OF THE INVENTION

In one embodiment the present invention comprises an electrosurgical device that includes an elongate surgical probe member having disposed about a portion of its outer surface dual cauterization electrodes that are electrically isolated from each other. In one embodiment the cauterization electrodes may be helically oriented about the outer surface of the probe member. A longitudinally oriented lumen extends through the member and is adapted to deliver a fluid through the member from a fluid source. The lumen has at least one outlet port, preferably at the distal end of the member, through which the fluid can be discharged. The device also includes a selectively deployable cutting electrode that is able to be retracted within the lumen when not in use, and to be extended from the lumen upon deployment. The fluid delivered through the lumen serves both to cool the cauterization electrodes during cauterization, and to irrigate the surgical site.

The device is used in conjunction with an electrosurgical generator that supplies electrosurgical energy to the cauterization electrodes and to the cutting electrode. Switches are provided to enable a surgeon to switch easily between the cutting and coagulation modes, and to selectively deliver fluid through the lumen at desired flow rates.

When used for cauterization the device can function in a bipolar mode with the dual cauterization electrodes being electrically isolated from each other. The device also may be used as a bipolar surgical device for performing cutting procedures with the cutting electrode serving to cut tissue, and one or both of the cauterization electrodes serving as return electrodes.

In another embodiment the device serves only as a cauterization probe and does not include a cutting electrode.

A control system associated with the device facilitates the control temperature of the energy delivering electrode (especially in the cauterization mode) to prevent excess heating of the electrode and/or the delivery to the electrode of excess energy. In one embodiment the temperature of the energy delivering electrodes is monitored and compared to a predetermined maximum temperature value. The flow rate of fluid delivered through the lumen is controlled, based upon the compared temperature values, to maintain electrode temperature at or below the predetermined value. Flow rate can be increased if the measured temperature exceeds the predetermined value. Similarly, flow rate can be maintained or decreased if the measured temperature equals or is below the predetermined value.

The energy output by the generator to the probe may also be controlled based on measured tissue impedance, in conjunction with the monitoring of electrode temperature. Upon delivery of energy to tissue, the impedance value is then compared to a predetermined maximum impedance value. If the measured impedance exceeds the predetermined impedance value, a signal is generated and transmitted to the generator to prevent further delivery of energy by the generator. This system serves as an added safety measure to prevent injury to a patient as a result of delivering too much energy through the probe or excessively heating tissue. The measured tissue impedance value may also be used to control the fluid flow rate, independent of temperature monitoring.

The device is useful for general surgical applications in which the cutting and cauterization probe directly accesses a target site through a percutaneous incision located proximal to the target site. In addition, the probe may be manufactured in dimensions suitable for use in microsurgical procedures where the probe can be delivered to the target during arthroscopic, endoscopic, or laproscopic surgery.

BRIEF DESCRIPTION OF THE DRAWINGS

FIG. 1 is a schematic view of an electrosurgical cutting and coagulation system constructed according to the present invention.

FIG. 2 is a perspective view of an electrosurgical probe useful with the system illustrated in FIG. 1.

FIG. 3A is a perspective view of a forward portion of the electrosurgical probe illustrated in FIG. 2.

FIG. 3B is a front end view of the probe illustrated in FIG. 3A.

FIG. 3C is a perspective view of the probe illustrated in FIG. 3A, with the cutting electrode in the retracted position.

FIG. 8 is schematic view of an electrosurgical cauterization system according to the present invention.

FIG. 9 is a perspective view of a forward portion of an electrosurgical cauterization probe useful with the system of FIG. 8.

FIG. 10 is a sectional view, allow lines 10—10 of the electrosurgical cauterization probe of FIG. 8.

DETAILED DESCRIPTION OF THE INVENTION

Figure 4:
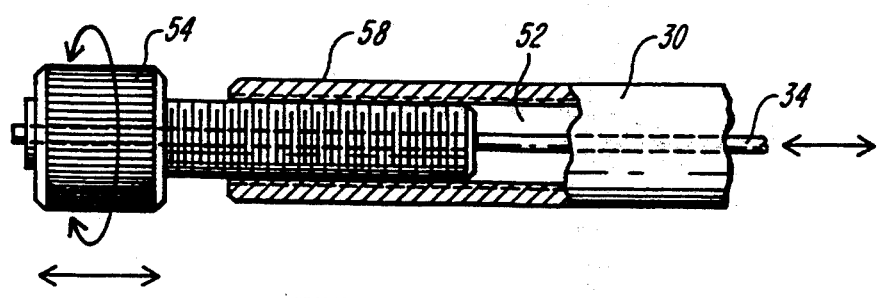
FIG. 4 is a side view partially cut away, of a rear portion of the electrosurgical probe of FIG. 2, illustrating a knob for controlling the extension and retraction of the cutting electrode.

FIG. 1 illustrates the electrosurgical cutting and coagulation system 10 of the present invention. The system 10 comprises a radio frequency energy source 12, a control unit 14, in electrical communication with the energy source, and an electrosurgical probe 16. The control unit 14 is in electrical communication with probe 16 through electrode leads 18, 20, 22. Further, a fluid source 24 communicates a fluid to probe 16 through conduit 26.

The electrosurgical cutting and cauterization probe 16 is further illustrated in FIGS. 2 through 3C. As illustrated, probe 16 has a handle portion 28 at its proximal end and an elongate member 30 that extends from the handle portion. The distal end of elongate member 30 is somewhat tapered and includes a cauterization tip 32 and a retractable cutting electrode 34. Cutting electrode 34 is able to extend from, or to be retracted within, a substantially circular orifice 36 which preferably is disposed in the distal end of cauterization tip 32. The exposed outer surface 33 of the cauterization tip 32 includes dual cauterization electrodes 38, 40. Preferably, cauterization electrodes 38, 40 are helically oriented about the surface 33 of cauterization tip 32. However, other orientations for electrodes 38, 40 are possible as well.

The handle portion 28 of probe 16 includes a fluid inlet port 42 that communicates with fluid source 24 through conduit 26. Electrode leads 20 and 22 emerge from a cuff 44 on the handle portion 28 of the probe. The proximal ends of leads 20, 22 have connectors 46, 48, which are matable with control unit 14. The distal ends of leads 20 and 22 connect to cauterization electrodes 38 and 40, respectively.

Cutting electrode 34 extends throughout the length of probe 16, and preferably has a length greater than the probe itself so that it is able to emerge both from the distal end of member 30 and the proximal end of handle 28. An electrode lead 18, having connector 50, connects the proximal end 34A of cutting electrode 34 to control unit 14. Cutting electrode 34 preferably is coated with an insulating material over its entire length, except for its extreme distal end which is uncoated so as to deliver electrosurgical energy to tissue. Suitable insulating materials include polymers such as polyvinylidene fluoride, polytetrafluoroethylene, fluorinated ethylene-propylene polymers, polyethylene, and others known to be suitable for use in medical applications.

Figure 5:
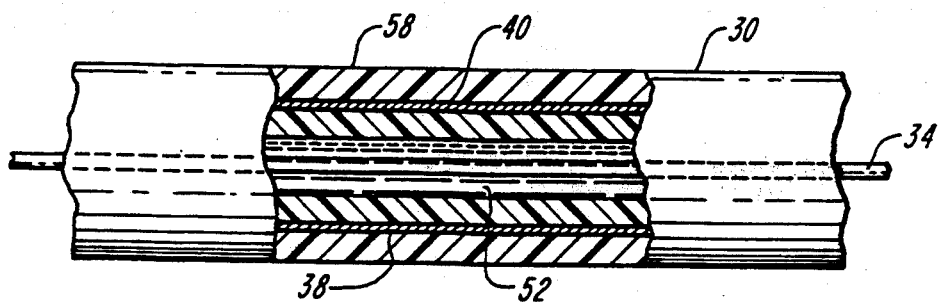
FIG. 5 is a side view, partially cut away, illustrating a portion of the electrosurgical probe of FIG. 2 constructed according to the present invention.
Figure 6:
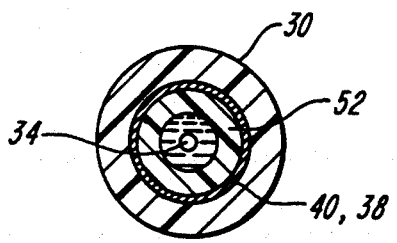
FIG. 6 is a sectional view along lines 6—6 of the probe illustrated in FIG. 3A.

Referring to FIGS. 4, 5, and 6, lumen 52 preferably is centrally located within probe 16 and extends throughout the length of the handle portion 28 and elongate member 30, along the longitudinal axis of the probe. The inlet port 42 provides a passageway for fluid to be communicated from conduit 26 to lumen 52. A fluid from source 24 is thus able to be communicated to inlet port 42 to enable fluid to be delivered through the lumen to the orifice 36 where it is discharged from the probe to contact tissue.

Figure 7:
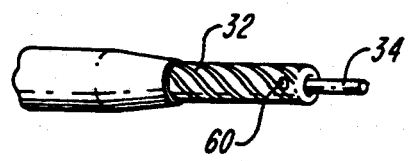
FIG. 7 is an alternative embodiment of the electrosurgical probe illustrated in FIG. 3A, having a side-mounted fluid outlet port.

In an alternative embodiment, illustrated in FIG. 7, a side-mounted orifice 60, in fluid communication with lumen 52, may be used to discharge fluid to adjacent tissue. Orifice 60 may be used alone, or in combination with orifice 36. Also, orifice 60 may, if desired, be paired with one or more additional side-mounted orifices (not shown).

As noted, cutting electrode 34 is positioned within and extends over the entire length of lumen 52. The selectively deployable nature of cutting electrode 34 is advantageous in that electrode 34 can be deployed for a cutting procedure and retracted during cauterization.

Deployment of electrode 34 can be controlled by a suitable mechanism preferably mounted on the handle portion 28 of probe 16. FIG. 4 illustrates a thumbscrew 54, mounted upon the proximal end of handle 28, which can be used to control the retraction and extension of the cutting electrode 34. Alternatively, as shown in FIG. 1, an excess length of electrode 34 may extend from the proximal end of handle 28 so as to be manually manipulated to regulate the length of electrode 34 extending from orifice 36. A variety of other length controlling mechanisms may be utilized as well.

In one embodiment cutting electrode 34 may be biased either to an extended or retracted position. The biasing force may be overcome by the mechanism used to control the extension/retraction of electrode 34.

The dimensions of the probe 16 are such that it is suitable for use in arthroscopic, endoscopic, laproscopic, and general surgery. Preferably, the length of the probe is approximately 10 to 18 inches. The diameter of member 30 can vary within a range of dimensions known in the art to be suitable for the intended use of the probe. In a preferred embodiment, the diameter is not constant along the entire length of member 30. Member 30 preferably has approximately three distinguishable but integral sections which have slightly differing diameters. As illustrated in FIG. 2, a proximal section 30A of the member 30 is the longest segment and has the largest diameter $D_1$. Adjacent this section is portion 30B of member 30, having a slightly smaller diameter $D_2$. The diameter of region 30C tapers over its entire length, terminating in cauterization tip 32 which has a diameter $D_3$. Generally, the diameter $D_1$ ranges from approximately 10 to 20 French (0.13 to 0.26 inch). Diameter $D_2$ ranges from 7 to 15 French while $D_3$ ranges from about 5 to 12 French.

The diameter of cutting electrode 18 can also vary, and its size depends to a large extent upon the diameter of lumen 52. One requirement of the lumen diameter is that it be sufficient to accommodate the flow of fluid while electrode 18 is disposed within the lumen. Generally, the lumen diameter is in the range of 3 to 7 French, while the diameter of electrode 34 ranges from 1 to 3 French.

The probe 16 of the present invention can be manufactured of a variety of materials, including polyolefins and nylons, that are known to be suitable for use in medical applications. The outer wall 58 of member 30 preferably is manufactured of an insulating polymeric material of the type well known in the art and suitable for use in medical applications.

The cutting electrode 34 and cauterization electrodes 38, 40 preferably are made from a highly conductive material such as gold, silver or platinum. The conductive material from which the electrodes are made can be a solid material or, alternatively, a plating which is deposited upon an insulating material such as a polymer. The cutting electrode should have sufficient rigidity, tensile strength and compressive strength to enable it to be extended from and retracted within the probe 16.

As noted, the probe 16 of the present invention is useful in general surgical procedures as well as in laproscopic, arthroscopic, and endoscopic surgical procedures. A significant advantage of probe 16 is that it represents a single instrument which can perform both cauterization and cutting procedures in a bipolar mode. Moreover, cauterization with probe 16 is more effective because the fluid flow through lumen 52 prevents electrodes 38 and 40 from transferring excessive thermal energy to tissue.

In operation, the probe may be inserted through an incision and directed to the location at which the surgical procedure is to be performed. Cutting electrode 34 can be extended from within lumen 52 once the probe reaches the surgical site. Thereafter, electrosurgical energy can be delivered between electrode 34 and one or both of electrodes 38, 40 (serving as return electrodes) to cut tissue. Control of bleeding can be effected utilizing cauterization tip 32 and cauterization electrodes 38 and 40. To do so, tip 32 is positioned in contact with tissue requiring cauterization and electrosurgical energy is delivered between electrodes 38 and 40 upon changing the mode of operation from cutting to coagulation, using, for example, switch 56 on control unit 14. This cauterization procedure can be bipolar in that one of electrodes 38 and 40 serves as an active, energy delivering electrode, while the other serves as a return electrode.

FIGS. 8 through 10 illustrate an alternative embodiment of the invention in which system 10 serves only to cauterize tissue. The probe is similar in construction to that illustrated in FIGS. 1 through 7, but it does not include a cutting electrode. Although lumen 52 is illustrated as being centrally disposed within member 30, it is understood that the lumen need not be disposed within member 30, but instead can be appended to member 30.

During cauterization procedures, and optionally during cutting as well, fluid is delivered through lumen 52 at a desired rate. The delivery of fluid serves two purposes. First, the fluid acts to limit the heat transfer from cauterization electrodes 38, 40 to adjacent tissue to an extent that tissue does not become overly heated by the electrodes, causing tissue and/or coagulant to stick to tip 32. This enables more effective and convenient cauterization. The fluid delivered to tissue can also serve as an irrigant to improve the visibility in the area subject to surgery and to remove any debris from the surgical site.

The fluid flow rate may be constant or variable. Preferably, the flow rate is variable and occurs only when energy is delivered to effect cauterization and preferably ranges from approximately 1 to 50 ml/minute. One skilled in the art will readily appreciate that it may be desirable to use a somewhat higher flow rate.

One of ordinary skill in the art will appreciate that the fluid flow rate depends on a number of variables, including the temperature of the fluid and the amount of power delivered to the cauterization electrode. The flow rate should be effective to control the temperature of the cauterization electrode, but should not be so high as to destroy tissue. The electrode temperature should be maintained below about 60° C., and more preferably below about 46° C. The temperature of the fluid may range from quite cold (e.g., about 4° C.) to about room temperature or higher (e.g., about, 27° C.).

Flow rate can be manually adjusted or can be controlled by one or more feedback mechanisms that monitor temperature impedance and/or electrode temperature. A suitable feedback mechanism is described below.

One skilled in the art will readily appreciate that certain surgical procedures will be able to tolerate more fluid flow while others will be able to tolerate less. The fluid flow rate can be adjusted to accommodate the requirements of a variety of surgical procedures.

The fluid source 24 may communicate with a valve or pump mechanism (not shown) which controls the flow rate of fluid through lumen 52. The flow rate can be constant at a predetermined rate, such as about 30 ml/minute, which generally is sufficient to limit the temperature of electrodes 38, 40 and cauterization tip 32.

The flow rate preferably is variable and is controlled through a feedback system that monitors electrode temperature and/or tissue impedance. The delivery of energy through electrodes 38 and/or 40 to cauterize tissue causes the temperature of the electrodes to rise significantly. Excess heating of the electrodes (e.g., above about 60° C.) can damage tissue and result in the buildup of excess coagulant on the cauterization tip 32 of probe 16. Such coagulant can impede the flow of current from tip 32 to tissue and thus must be removed to enable effective energy delivery to tissue.

Figure 11:
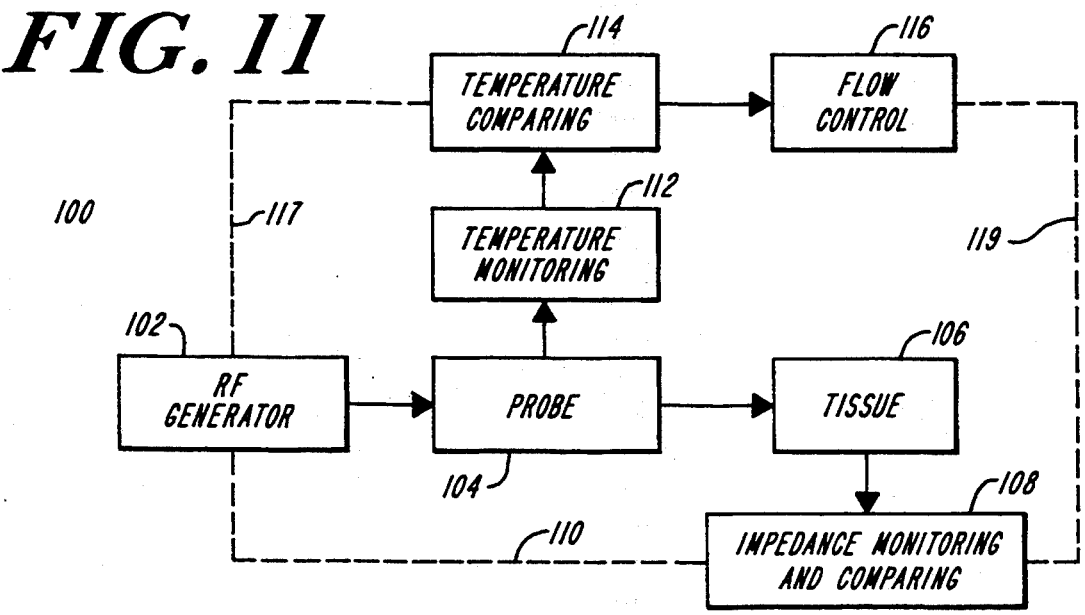
FIG. 11 is a block diagram illustrating the temperature and impedance feedback control system of the invention.

The present invention utilizes a feedback system 100, illustrated in FIG. 11, that monitors electrode temperature and/or tissue impedance to control the flow rate of fluid through lumen 52. The fluid passing through the lumen serves to cool electrodes 38, 40, and flow rate of the fluid affects electrode temperature. FIG. 11 is a block diagram that illustrates the operation of feedback system 100. As illustrated, generator 102 delivers electrosurgical energy to probe 104 which, in turn, conveys the energy to tissue 106. Impedance of the tissue is measured through a circuit 108, preferably associated with the generator, based on the energy applied to the tissue. Circuit 108 compares the measured impedance with a predetermined maximum impedance value. If the measured impedance exceeds the predetermined maximum impedance a disabling signal 110 is transmitted to generator 102 to cease further delivery of energy to probe 104. Alternatively, the measured impedance, as compared to a predetermined desired impedance value, can also be used to control the fluid flow rate through the probe 104 to avoid excessive heating of energy delivering electrodes.

Feedback system 100 preferably monitors electrode temperature contemporaneous with the monitoring of tissue impedance. In a preferred embodiment the tissue impedance monitoring circuit is used to disable the generator (if necessary) while a temperature monitoring function facilitates control of fluid flow rates.

As electrosurgical energy is delivered to tissue 106 from probe 104, the electrode temperature is monitored by element 112, which may be a thermistor, thermocouple, or the like. Comparator 114 compares the measured electrode temperature value with a predetermined maximum temperature value. Flow control element 116 regulates the fluid flow rate to achieve optimal electrode temperature based on the measured electrode temperature in relation to the predetermined maximum temperature. For example, if the measured electrode temperature exceeds the predetermined maximum temperature, flow rate will be increased. Similarly, if the measured temperature is low, flow rate will be maintained or decreased.

Further, output 117 from the temperature comparator 114 can be input to generator 102 to regulate the amount of power delivered by the generator, thus controlling temperature. Similarly, output 119 from impedance monitor and comparator 108 can be inputted to flow regulator 116 to regulate fluid flow and thus control electrode temperature.

Figure 12:
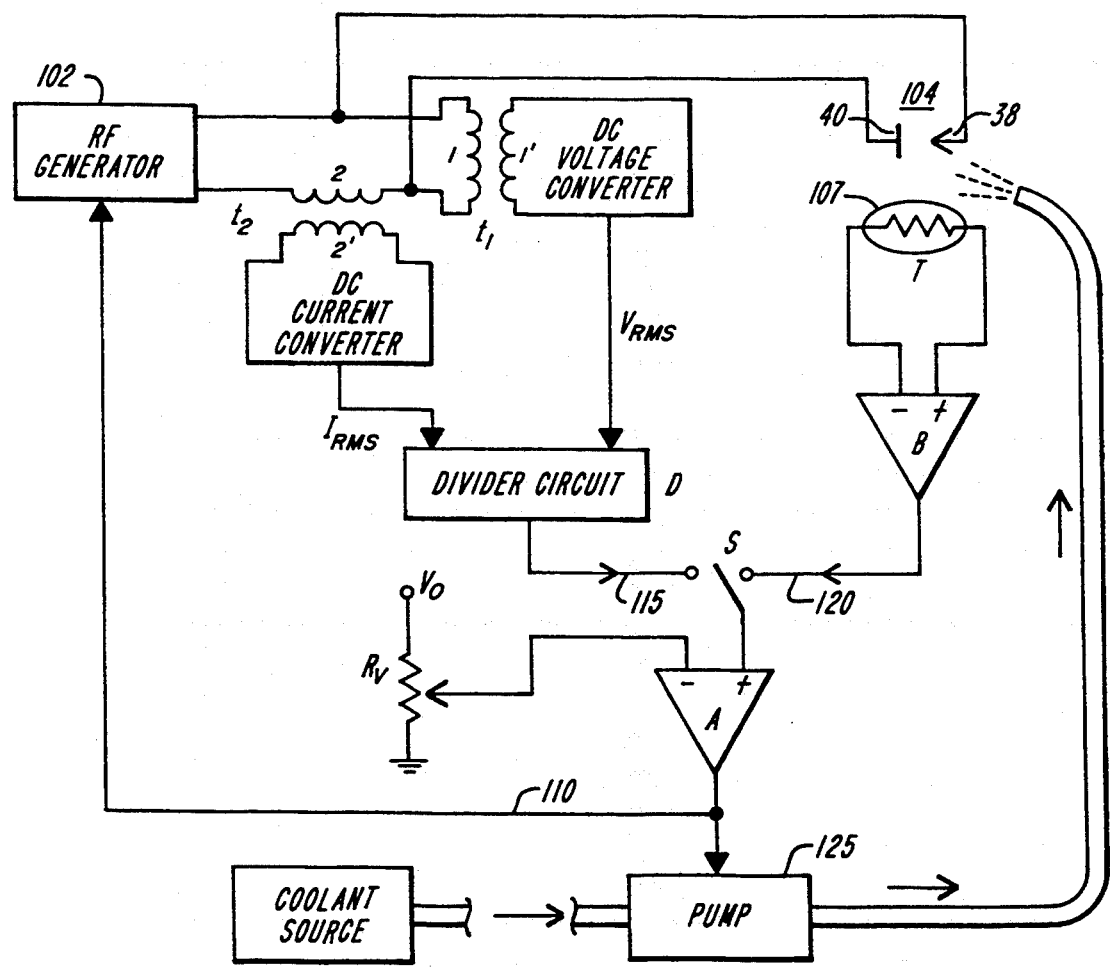
FIG. 12 illustrates a circuit useful in implementing the temperature and impedance feedback control system of the invention.

Although one having ordinary skill in the art will appreciate that the feedback system of the invention can be implemented in a variety of ways, an exemplary feedback circuit is illustrated in FIG. 12.

FIG. 12 depicts an exemplary circuit to effect the system described in FIG. 11. An energy delivering means, such as RF generator 102, is transformer coupled to the probe 104, to apply a biologically safe voltage to a patient'S tissue. In this embodiment, the probe is represented as a bipolar cauterization probe 104 having an energy delivering electrode 38 and a ground electrode 40. Both electrodes 38, 40 are connected to the primary side of the transformer windings 1, 2. The common primary winding 1, 2 is magnetically coupled via a transformer core to the secondary windings 1', 2' so that the current and voltage of the primary side is reflected to the secondary windings 1', 2'.

According to a preferred aspect of the invention, the primary windings 1 of the first transformer $t_1$ couple the output voltage of the probe 104 to the secondary windings 1'. The primary windings 2 of the second transformer $t_2$ couple the output current of the probe 104 to the secondary windings 2'. Those of ordinary skill in the art will appreciate that the two transformers act as step-down transformers and further serve as means of isolating the high voltage between the electrosurgical probe 102 and the secondary windings or measuring circuit 1', 2'.

The measuring circuits determine the root mean square (RMS) values or magnitudes of the current and voltage and these values, represented as voltages, are inputted to a dividing circuit D to geometrically calculate, by dividing the RMS voltage value by the RMS current value, the impedance of the body tissue at the probe electrode 104. Those of ordinary skill in the art will understand that the voltage presented at the output of the divider circuit D is representative of and a function of the impedance of the tissue adjacent to the probe electrodes 38, 40.

The output voltage of the divider circuit D is presented at the positive(+) input terminal of comparator A. A voltage source $V_o$ supplies a voltage across the variable resistor $R_v$, thus allowing one to manually adjust, via a knob, the voltage presented at the negative input of comparator A. This voltage represents a maximum impedance value beyond which power will not be applied to the probe 104. Specifically, once the tissue is heated to a temperature corresponding to an impedance value greater than the maximum cut-off impedance, the RF generator 102 will stop supplying power to the probe 104. Comparator A can be of any commercially available type that is able to control the amplitude or pulse width modulation of the RF generator.

In one aspect of the invention, the flow rate of the coolant can be controlled by either the tissue impedance, as represented by signal t15, or by the probe temperature, as represented by signal 120. In one preferred embodiment, the switch S is activated to allow the impedance signal 115 to enter the positive(+) input terminal of comparator A. This signal along with the reference voltage applied to the negative(−) input terminal actuates the comparator A to produce an Output signal. If the tissue is heated to a biologically damaging temperature, the tissue impedance will exceed the selected impedance value seen at the negative(−) input terminal thereby generating a signal 110 to disable the RF generator 102, ceasing the power supplied to the probe 104.

The output signal of comparator A can further be communicated to pump 125. If the temperature of the probe 104 is high, despite the tissue impedance falling within acceptable limits, the pump 125 will adjust the rate of flow of the cooling fluid subsequently applied to the probe electrodes 38, 40 to decrease the probe temperature. Thus, the output signal of comparator A may either disable the RF generator's 102 power output (depending on the tissue temperature as reflected by its impedance) or cool the probe or perform both operations simultaneously.

In another aspect of the invention, the rate of flow of the cooling fluid is controlled by the temperature measured at the catheter tip. The switch S is actuated so as to transfer to the positive(+) input terminal of comparator A the comparator B output signal 120. The temperature sensor is a thermistor T, and is preferably disposed longitudinally along the outside body of probe 104. The thermistor T senses temperature and reacts to differential temperature changes in a predictable manner. Thus, the thermistor actively reflects through varying resistance the temperature it is exposed to.

Both leads of the temperature sensitive thermistor T are inputted to the positive(+) and negative(−) terminals of comparator B to produce a signal 120 indicative of the catheter temperature. This signal 120 works in conjunction with the reference voltage inputted at the negative(−) terminal to activate the comparator A to produce an output signal that is electrically communicated to the pump 125. The pump 125 in response to the signal selectively varies the flow rate of the cooling fluid as it travels through a lumen 52 disposed within the probe 104 to the energy delivering electrode 38.

It is understood that the temperature of the electrode can be continuously monitored or randomly sampled to ensure against excessive heating of the tissue. Moreover, the pump employed can be a valve, or series thereof, rather than an electrical-mechanical apparatus. The valve can adjust the rate of flow of the cooling liquid from the fluid supply source in the same manner as a pump.

Virtually any generator able to provide electrosurgical energy for medical applications may be used with the present invention. Preferably, the generator 12 is a voltage determinative, low source impedance generator that provides radio frequency energy. A preferred generator is able to supply up to 3 amps of current and has an impedance value of less than 10 ohms.

The energy supplied by the generator to the control unit 14 and to probe 16 is preferably in the radio frequency (RF) range. Although virtually any frequency in the RF range may be supplied to probe 16, the preferred range is about 500 to 700 KHz, and most preferably about 550 KHz.

As illustrated in FIG. 1, RF energy is provided to a control unit 14 from a generator 12. The control unit 14 includes switching mechanism 56 which enables a surgeon to control to mode of operation of the probe. Moreover, additional switches (not shown) mounted on or remote from unit 14 may be used to control the delivery of energy and the magnitude of the delivered energy.

The energy requirements of the probe are dynamic and will vary upon the impedance value of tissue which is being treated, and upon whether the tissue is being coagulated or cut. The impedance of tissue varies among tissue types and the amount of blood present in or around the tissue. The amount of current delivered by the probe to tissue thus depends on the impedance of the tissue. Where the tissue contacted has a lower impedance value, more current will be delivered to the tissue through the clip, and, conversely, less current will be delivered where the tissue has a higher impedance value. The current delivered during cutting procedures utilizing electrode 34 generally ranges between 0.2 amps and 3 amps. The voltage applied to tissue for such cutting procedures is between about 60 and 1000 volts rms. Current delivered during coagulation is generally in the range of 0.25 to 1.0 amp., and coagulation voltages is in the range of about 10 volts to about 50 volts rms.

It is understood that various modifications may be made to the invention described above without departing from the scope of the claims. For example, rather than operating in the bipolar mode, the cutting and coagulation each may be performed in a monopolar mode with the use of a remote ground pad. Also, the mode of operation may be controlled by the use of a foot pedal rather than a switch mounted on control unit 14.

What is claimed is:

1. A method for controlling the temperature of an energy delivering, cauterizing electrode, comprising:

providing an elongate electrosurgical probe member having disposed at a distal portion of an outer surface thereof at least one energy delivering cauterization electrode, the probe member having a fluid delivering lumen associated therewith and being in electrical communication with an electrosurgical generator unit;

delivering electrosurgical energy from the generator unit through the probe member to the energy delivering electrode and adjacent tissue;

measuring the tissue impedance based on the energy applied thereto and generating a signal representative of measured tissue impedance;

comparing the measured tissue impedance with a predetermined maximum impedance value;

transmitting to the electrosurgical generator unit a signal to cease or limit further energy delivery if the measured tissue impedance exceeds the predetermined maximum impedance value;

passing a fluid through the lumen at a desired flow rate to regulate the temperature of the energy delivering electrode; and regulating the flow rate to maintain the tissue impedance at or below the predetermined maximum impedance value.

2. The method of claim 1 wherein the flow rate is in the range of 1 to 50 ml/minute.

3. The method of claim 1 further including the step of increasing the flow rate when the measured tissue impedance value exceeds the predetermined maximum impedance value.

4. A system for controlling the temperature of an energy delivering, cauterizing electrode, comprising:

an elongate electrosurgical probe member having a central lumen disposed therein to enable fluid to be conveyed through the probe member for discharge at a distal portion of the probe member, the probe member having at least one energy delivering electrode disposed at a distal portion of the probe member;

an electrosurgical generator unit in electrical communication with the probe member for supplying electrosurgical energy to the electrode for delivery to tissue adjacent to the electrode;

a fluid supply source in communication with the lumen;

impedance measuring means for measuring tissue impedance based on the energy applied thereto;

impedance comparing means for comparing the measured tissue impedance to a predetermined maximum impedance value, the impedance comparing means generating a disabling signal if the measured impedance value exceeds the predetermined maximum impedance value;

means for communicating the disabling signal to the electrosurgical generator unit to cease further delivery of energy from the generator unit to the probe member; and fluid control means for regulating the rate of flow of fluid through the lumen to maintain the measured tissue impedance at or below a predetermined maximum impedance value.

* * * * *